(12) United States Patent
Hayashi et al.

(10) Patent No.: US 6,652,102 B2
(45) Date of Patent: Nov. 25, 2003

(54) VISUAL FUNCTION TEST APPARATUS

(75) Inventors: Akihiro Hayashi, Toyokawa (JP);
Noritsugu Nozawa, Toyokawa (JP);
Yuichiro Kanazawa, Gamagori (JP);
Hidetaka Hoshino, Nukata-gun (JP)

(73) Assignee: Nidek Co., Ltd, Gamagori (JP)

( * ) Notice: Subject to any disclaimer, the term of this patent is extended or adjusted under 35 U.S.C. 154(b) by 204 days.

(21) Appl. No.: 09/977,299

(22) Filed: Oct. 16, 2001

(65) Prior Publication Data

US 2002/0047997 A1 Apr. 25, 2002

(30) Foreign Application Priority Data

Oct. 20, 2000  (JP) ........................................ 2000-327010

(51) Int. Cl.[7] ............................................... A61B 3/02
(52) U.S. Cl. ..................................................... 351/243
(58) Field of Search ........................... 351/222, 239–246

(56) References Cited

U.S. PATENT DOCUMENTS

| | | | |
|---|---|---|---|
| 4,155,632 A | * | 5/1979 | Wolbarsht .................... 351/243 |
| 4,550,990 A | * | 11/1985 | Trispel et al. ............... 351/243 |
| 5,485,231 A | | 1/1996 | Hayashi et al. |
| 5,629,748 A | | 5/1997 | Hayashi et al. |
| 5,825,460 A | | 10/1998 | Kohayakawa |
| 5,835,191 A | | 11/1998 | Mura |
| 5,886,823 A | | 3/1999 | Sugano |
| 6,139,151 A | | 10/2000 | Ueno et al. |
| 6,149,272 A | | 11/2000 | Bergner et al. |

FOREIGN PATENT DOCUMENTS

| | | |
|---|---|---|
| JP | 11-9550 A | 1/1999 |
| JP | 2000-126131 A | 5/2000 |
| JP | 2000-287925 A | 10/2000 |

* cited by examiner

*Primary Examiner*—George Manuel
*Assistant Examiner*—John R Sanders
(74) *Attorney, Agent, or Firm*—Oliff & Berridge, PLC (57) ABSTRACT

A visual function test apparatus for testing a visual function by presenting an optotype to an examinee's eye is disclosed. This apparatus includes a first half mirror disposed on a projection optical axis of light of the optotype; an illumination light source having a projection optical axis which is made substantially coaxial with the projection optical axis of the optotype light by the first half mirror; a concave mirror which reflects an illumination light from the illumination light source and the optotype light; a second half mirror disposed between the first half mirror and the concave mirror, the second half mirror reflecting the optotype light and the illumination light both reflected by the concave mirror toward the examinee's eye; and a control section which changes a ratio between a light quantity of the optotype light and a light quantity of the illumination light in accordance with a predetermined contrast ratio.

15 Claims, 9 Drawing Sheets

VISUAL FUNCTION TEST APPARATUS

BACKGROUND OF THE INVENTION

1. Field of the Invention

The present invention relates to a visual function test apparatus for examining visual functions of an examinee's eye.

2. Description of Related Art

A contrast sensitivity test in which optotypes of different contrasts are presented to an examinee has been performed as one of visual function tests. This contrast sensitivity test is important for examination of a visual function, in particular, a form sensitivity ability. A chart used in a conventional test for contrast sensitivity is constructed of a panel such as paper on which stripes with different frequencies, in several kinds of contrast ratios, are drawn. Furthermore, the contrast sensitivity test is conducted using an apparatus designed specifically therefor.

The chart made of a paper panel or the like, which is large as a whole, requires a large space sufficient to put up the chart on a wall or the like. Since the chart is used as put up an the wall or the like, the test is susceptible to ambient light.

Moreover, the apparatus designed specifically for contrast sensitivity test is not sufficiently provided with other visual acuity test systems. To make various kinds of visual function tests with respect to an examinee's eye, an optometer and other devices need separately preparing. In this case, an additional space is required to place the plural devices, which may make the test troublesome.

SUMMARY OF THE INVENTION

The present invention has been made in view of the above circumstances and has an object to overcome the above problems and to provide a visual function test apparatus that is space-saved and capable of examining plural visual functions such as a contrast sensitivity test, a visual acuity test, on a standalone basis.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a visual function test apparatus for testing a visual function by presenting an optotype to an examinee's eye, the apparatus including: a first half mirror disposed on a projection optical axis of light of the optotype; an illumination light source having a projection optical axis which is made substantially coaxial with the projection optical axis of the optotype light by the first half mirror; a concave mirror which reflects an illumination light from the illumination light source and the optotype light; a second half mirror disposed between the first half mirror and the concave mirror, the second half mirror reflecting the optotype light and the illumination light both reflected by the concave mirror toward the examinee's eye; and a control section which changes a ratio between a light quantity of the optotype light and a light quantity of the illumination light in accordance with a predetermined contrast ratio.

According to another aspect of the present invention, there is provided a visual function test apparatus for testing a visual function by presenting an optotype to an examinee's eye, the apparatus including: a concave mirror which reflects light of the optotype; a half mirror which reflects the optotype light reflected by the concave mirror toward the examinee's eye; an illumination light source having a projection optical axis which is made substantially coaxial with a projection optical axis of the optotype light by the half mirror; and a control section which changes a ratio between a light quantity of the optotype light and a light quantity of an illumination light from the illumination light source in accordance with a predetermined contrast ratio.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention In the drawings.

DETAILED DESCRIPTION OF THE PREFERRED EMBODIMENTS

Figure 1:
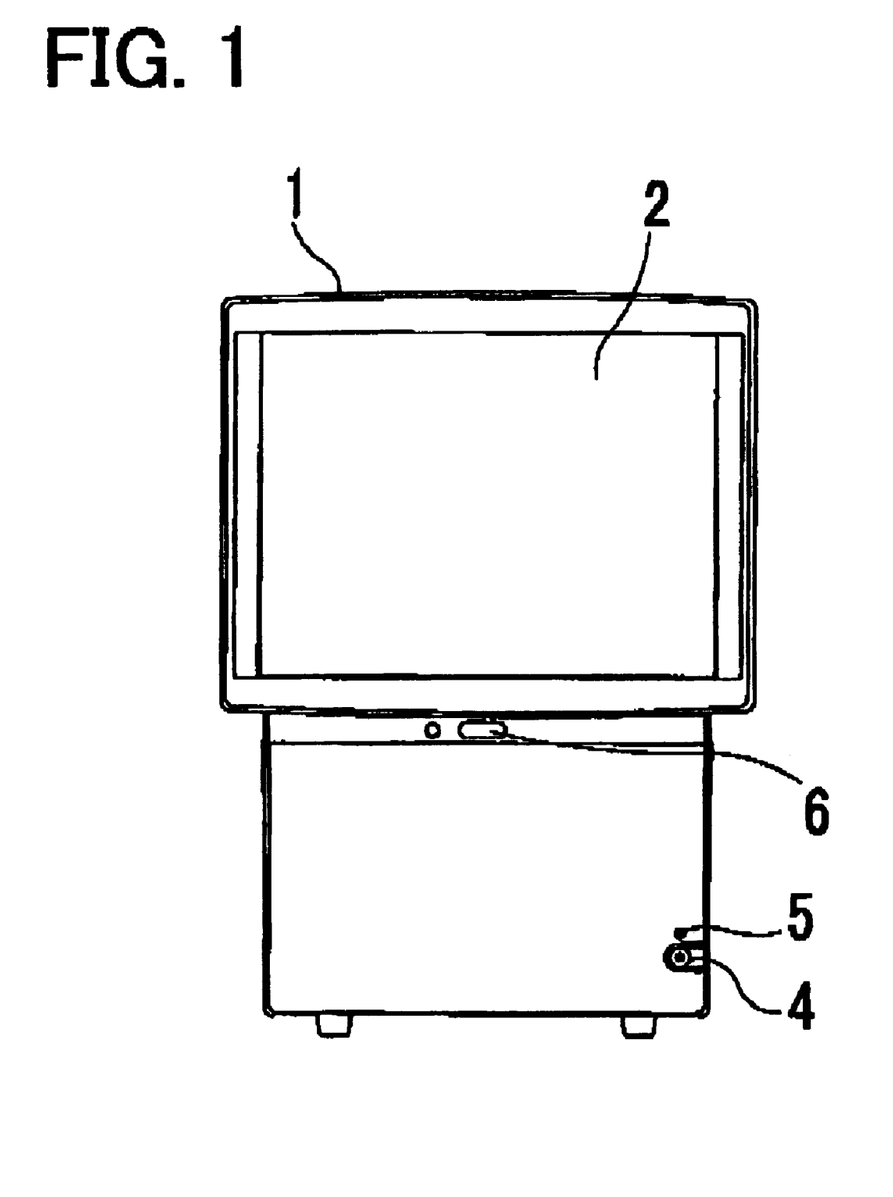
FIG. 1 is a perspective front view of a main unit of a visual function test apparatus in an embodiment according to the present invention.

A detailed description of a preferred embodiment of a visual function test apparatus of a space-saving type embodying the present invention will now be given referring to the accompanying drawings. FIG. 1 is a perspective front view of the apparatus in the present embodiment.

Numeral 1 is a main unit of the apparatus which is provided with a glass window 2 at an upper front part. This window 2 is applied with an antireflective film. An examinee looks at an optotype appearing in the center of the window 2. The window 2 may be constructed of a filter instead of a glass plate. The inside of the main unit 1 is painted black in order to make the interior structure hard to look by the examinee. Numeral 4 is a power switch and 5 is an indication lamp which lights up when the apparatus is powered on. Numeral 6 is a transmission and reception window which passes a pulse signal of infrared light issued from a remote control unit 50 mentioned later into the main unit 1 so that the signal (light) is received by a light-receiving part 72 (see FIG. 5) disposed in the main unit 1.

Figure 2:
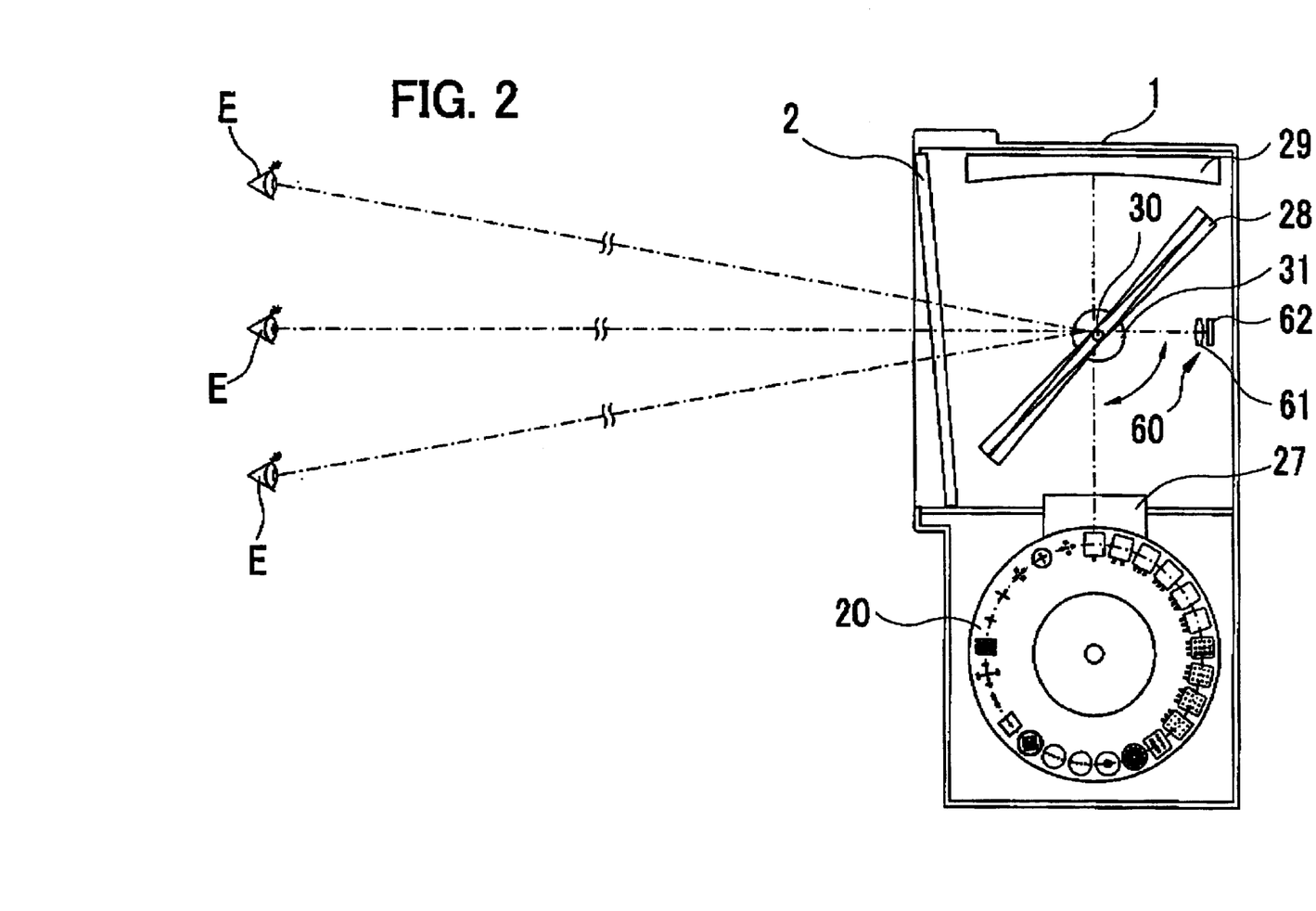
FIG. 2 is a side view of the apparatus seen through a side wall to show an optical system mounted therein.
Figure 3:
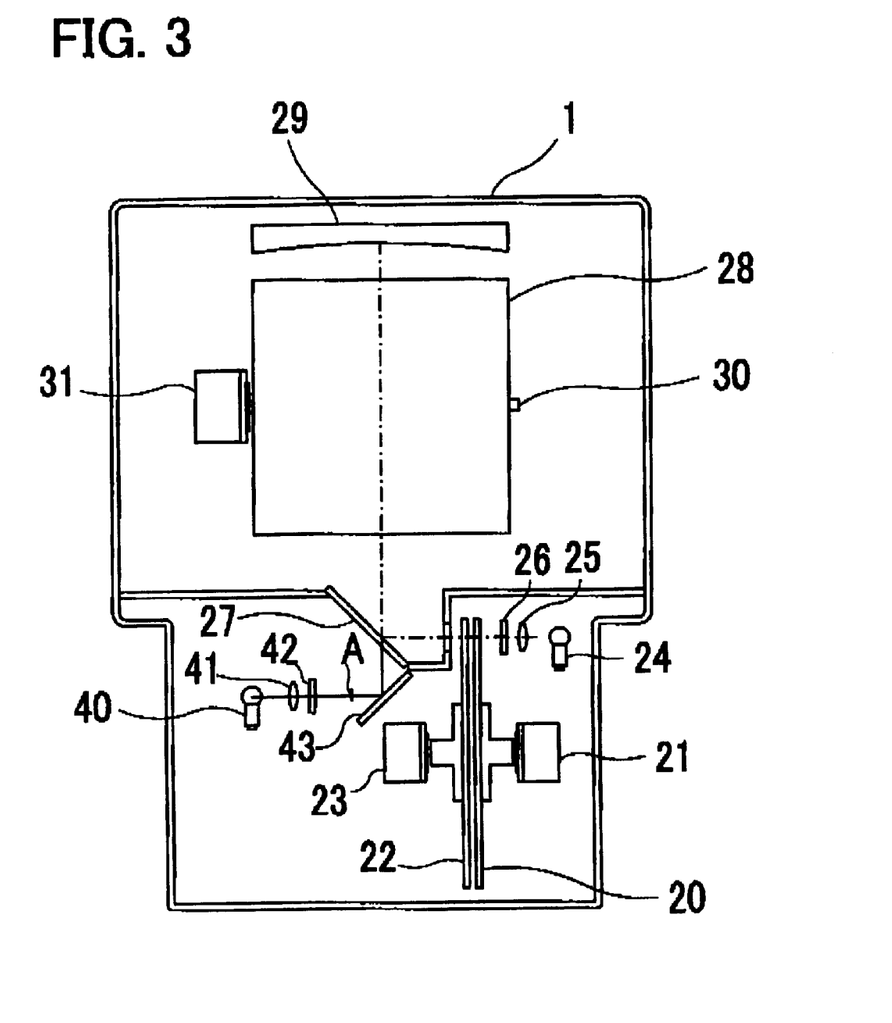
FIG. 3 is a front view of the apparatus seen through a front wall to show the optical system.

An optical system arranged in the main unit 1 is explained below with reference to FIGS. 2 and 3. FIG. 2 is a right side view of the main unit 1 seen through a side wall to show the optical system. FIG. 3 is a front view of same through a front wall.

An alphabet E indicates an eye to be examined. Numeral 20 is an optotype disc (chart disc) made of a glass plate, on which many test optotypes including plural optotypes of visual acuity values of 0.06–2.0 are provided in a circle by chrome evaporation and the like. This optotype disc 20 is rotated by a motor 21 to change an optotype (optotypes) to be presented to the examinee. Numeral 22 is a mask disc for masking a part of the optotypes to be presented. The mask disc 22 is rotated by a motor 23 to cover a desired part of the optotypes.

Numeral 24 is an illumination lamp for illuminating an optotype (optotypes); 25, a condenser lens; 26, a semitransparent diffusing plate; 27, a half mirror (beam combiner); 28, a half mirror (beam splitter); and 29, a concave mirror. A preferable one as the half mirror 27 has a reflecting surface applied with a metallic half mirror coating thereon in order to prevent light from being colored due to angle dependence. Also, the half mirror 28 may be constructed as with the half mirror 27.

The concave mirror 29 in the present embodiment is designed with a focal distance determined so that the optical distance between the optotype and the eye E may become a test distance of 5 meters when the distance between the eye E and the window 2 is 1.1 meters. Light of an optotype illuminated by the lamp 24 passes through the condenser lens 25 and the diffusing plate 26. A part of the light is then reflected by the half mirror 27 upward, passing through the half mirror 28, and is reflected by the concave mirror 29. The reflected optotype light is partly reflected by the half mirror 28 toward the eye E through the window 2. The half mirror 28 is attached to a rotating shaft 30 disposed on an axis perpendicular to an optical axis along which the optotype light is projected. When the rotating shaft 30 is rotated by a motor 30, the inclination angle of the half mirror 28 is changed. Accordingly, the optical path of the optotype light reflected by the half mirror 28 is changed in a vertical direction to thereby adjust the optotype light to the level of the eye E.

Numeral 40 is an illumination lamp for illuminating the background of an optotype image (virtual image) presented to the eye E. Numeral 41 is a condenser lens; 42, a semitransparent diffusing plate; and 43, a total reflection mirror. The diffusing plate 42 is located, when seen from the eye E side, at the rear (the lamp 40 side) of the position A conjugated with an optotype provided on the optotype disc 20 with respect to the concave mirror 29. This allow the diffusing surface of the diffusing plate 42 to be looked as magnified, providing a sufficient area to illuminate the background of the optotype presented to the eye E even if a small plate is used as the diffusing plate 42, thereby covering a deviation of the visual line of eye E. It is to be noted that the diffusing plate 42 may be placed at the position A.

Light from the illumination lamp 40 illuminates the condenser lens 41 and the diffusing plate 42 in turn. The illumination light diffused by the diffusing plate 42 is reflected upward by the mirror 43, combined with the optotype light through the half mirror 27, so that the projection optical axis of the illumination light and that of the optotype light are made substantially coaxial. The illumination light then passes through the half mirror 28 and is reflected by the concave mirror 29. The illumination light reflected by the concave mirror 29 is partly reflected by the half mirror 28 toward the eye E through the window 2.

Then, when the ratio between the light quantity of the lamp 24 and that of the lamp 40 is changed, the contrast of an optotype presented to the eye E can be changed (the details thereof will be mentioned later).

Numeral 60 is a detection optical system for detecting the level of the eye E. This optical system 60 is constructed of a light condensing lens 61 and a two-dimensional position detecting element 62. The optical system 60 is arranged on either side of the window 2 in the main unit 1. The condensing lens 61 condenses an infrared pulse signal emitted from a transmission and reception part 56 of the remote control unit 50 mentioned later onto the position detecting element 62, which generates an output signal to detect the level of the eye E. A detailed method of adjusting the optical path of optotype light to the level of an examinee's eye is referred to U.S. Pat. No. 5,485,231 corresponding to Japanese patent unexamined publication No. 7-236612.

Figure 4:
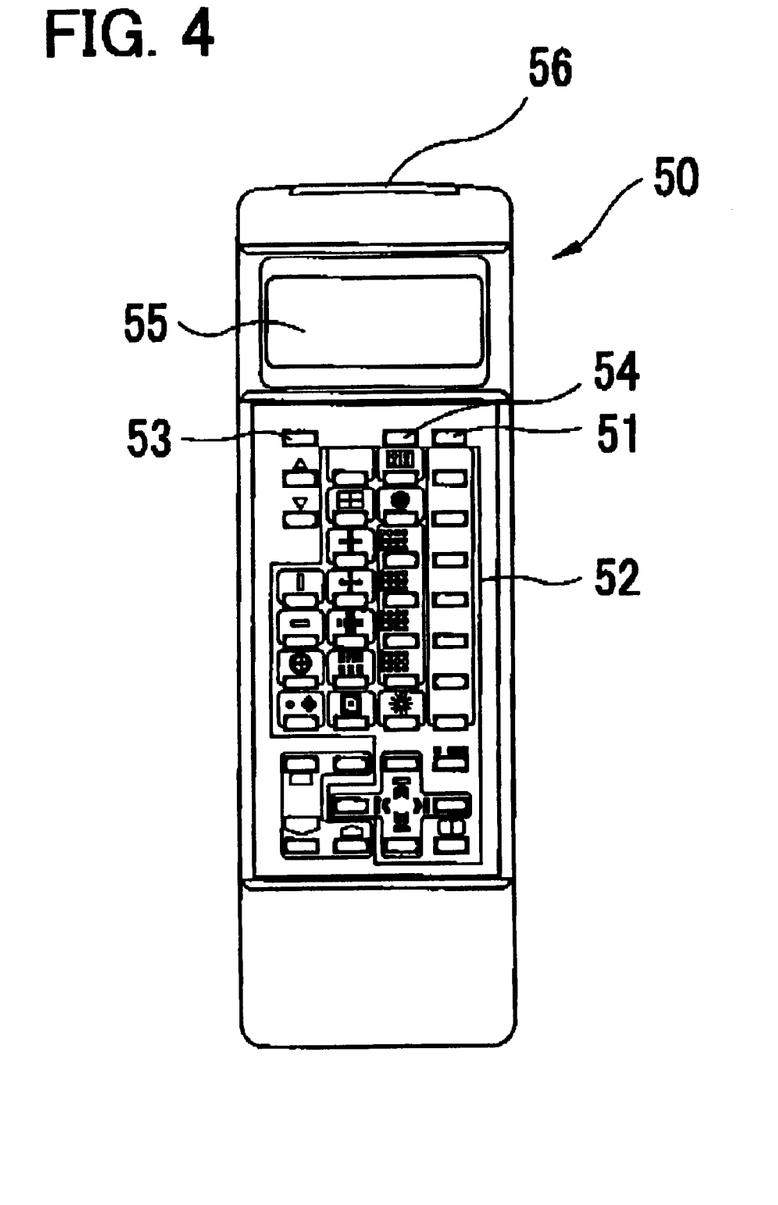
FIG. 4 is a plane view of a remote control unit of the apparatus in the embodiment, showing various switches on the unit.

FIG. 4 is a remote control unit 50 with which an examiner changes an optotype, turns on the lamp 40 for background illumination, and other operations to control the apparatus. Numeral 51 is a power switch; 52, a group of optotype selecting switches to be used for selecting an optotype (optotypes) of a desired visual acuity value and masking a part of the selected optotypes; and 53, a position transmission switch for transmitting an infrared pulse signal for position detection. Numeral 54 is a contrast change switch for turning on the lamp 40 to change the contrast of the presented optotype. The setting of a contrast ratio can be selected from among 100%, 25%, 12%, and 6% (the details will be described later). Numeral 55 is a display part for displaying the optotype to be presented in the main unit 1. The remote control unit 50 is also provided, on a front end thereof (namely, an upper end in the figure), with the transmission and reception part 56 for transmitting and receiving an infrared pulse signal.

Figure 5:
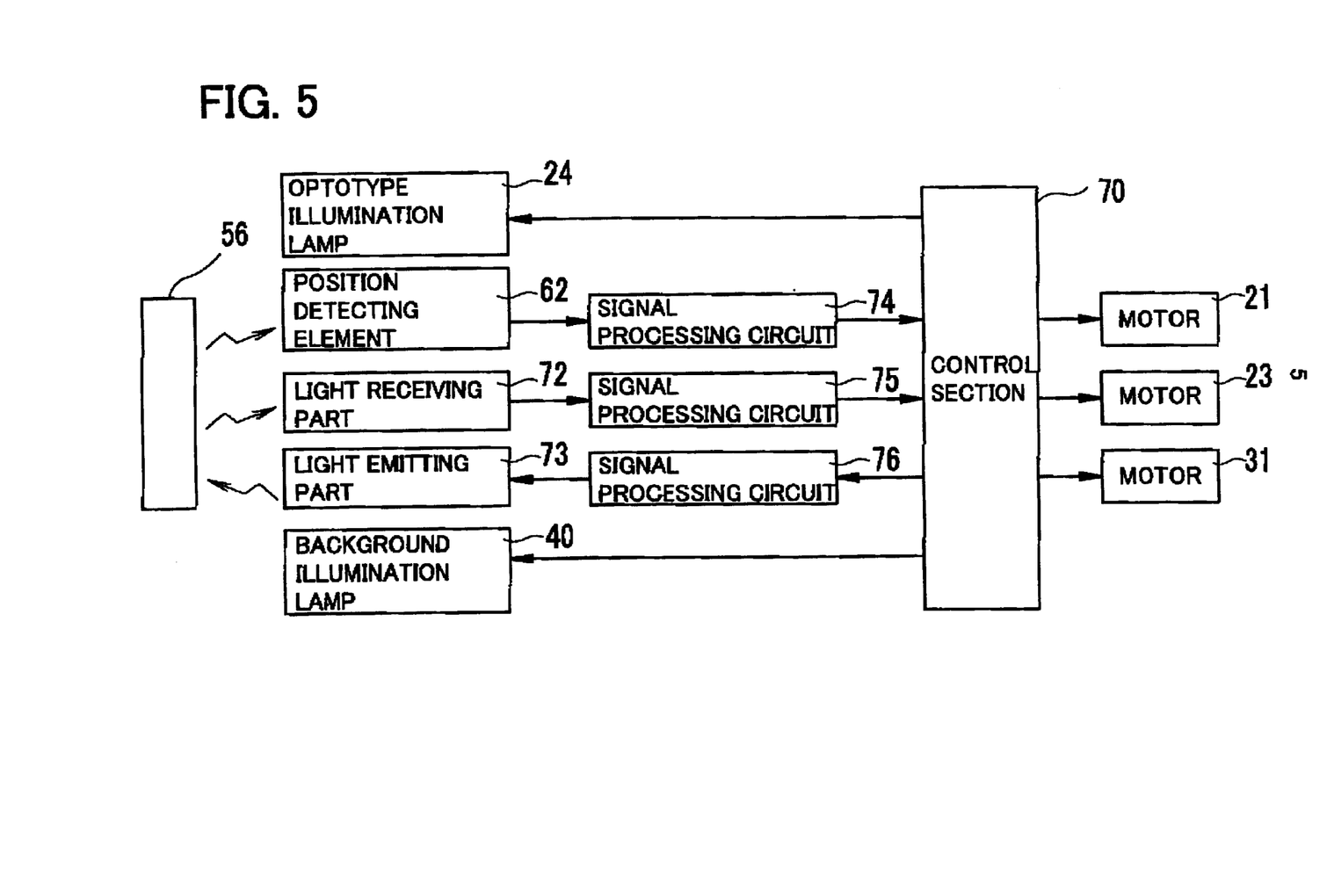
FIG. 5 is a block diagram of an electric system in the apparatus.

Operation of the apparatus constructed as above will be explained below with reference to a block diagram of an electric system in FIG. 5. In the following explanation, both a normal visual acuity test and a contrast sensitivity test are mentioned.

An examiner instructs an examinee to sit in place in front of the main unit 1 so that the distance between the examinee and the window 2 is 1.1 meters in the present embodiment. The examiner presses the switch 4 to turn on the power of the main unit 1. Upon power-on, a control section 70 drives the motors 21, 23, and 31 to set the optotype disc 20, the mask disc 22, and the half mirror 28 respectively in each initial position.

Subsequently, the examiner presses the switch 51 of the remote control unit 50, holds the unit 50 at the level of the eye E, aims the transmission and reception part 56 at the main unit 1, and then presses the switch 53. Upon press of the switch 53, an infrared pulse signal is emitted from the transmission and reception part 56 of the remote control unit 50. This infrared pulse signal is received by the light-receiving part 72 through the transmission and reception window 6, and is subjected to a predetermined processing in a signal processing circuit 75.

The processed signal is input in the control section 70. In response to the signal, the control section 70 puts the position detecting element 62 in a signal receiving state. Thus, the infrared pulse signal sent from the remote control unit 50 is detected by the position detecting element 62.

An output signal from the position detecting element 62 is input in the control section 70 through a signal processing circuit 74. The control section 70 obtains data on the position of the eye E in a vertical direction. Based on the positional data, the control section 70 drives the motor 31 to rotate by a corresponding amount. The rotation of the motor 31 changes the inclination angle of the half mirror 28 to adjust the optical path of the optotype light to the level of the eye E.

After the optotype light is exactly made incident on the eye E, the examiner operates the remote control unit 50 to perform a visual acuity test. The examiner presses one of the optotype selection switches 52 to select an optotype to be presented. A signal representing the information on the selected optotype is transmitted from the transmission and reception part 56 and received by the light-receiving part 72. The control section 70 then drives the motor 21 to place the optotype corresponding to the received signal in the optical path.

Furthermore, the control section 70 transmits the information on the presented optotype from a light emitting part 73 via the signal processing circuit 76. The transmitted signal representing the optotype information is received by the transmission and reception part 56 of the remote control unit 50 side. The thus received optotype information is displayed on the display part 55 in order to prevent a discrepancy from arising between the displayed content and the presented optotype. The examiner sequentially changes optotypes of different visual acuity values and examines the visual acuity of the eye E while asking the examinee if he can see the presented optotype.

To switch the test to the contrast sensitivity test, the examiner selects an optotype to be presented with a desired one of the switches 52 of the remote control unit 50 and then presses the switch 54 to change the contrast ratio of the selected optotype. Every time the switch 54 is pressed, the contrast ratio is changed to 100%, 25%, 12%, and 6% in turn.

Upon press of the switch 54, a corresponding infrared pulse signal is sent from the transmission and reception part 56 of the remote control unit 50. The infrared pulse signal is received by the light-receiving part 72 through the transmission and reception window 6, and subjected to a predetermined processing in the signal processing circuit 75, and then input in the control section 70. In response to this signal, the control section 70 causes the lamp 40 to light up at a predetermined light quantity. As with the change of optotypes, the information on the change in contrast ratio is displayed on the display part 55. The light emitted from the lamp 40 is partly reflected by the half mirror 28 toward the eye E. Simultaneously, the control section 70 causes the lamp 24 to reduce the illumination quantity to a predetermined quantity. Accordingly, the contrast ratio of the optotype image presented to the eye E is changed. The examiner sequentially changes optotypes of different visual acuity values and the contrast ratio of each optotype and examines the contrast sensitivity based on the response from the examinee as to if he can see the presented optotype.

Next, the contrast ratio of the optotype image as mentioned above is explained. Contrast changes are made by changing each light quantity of the lamp 24 and the lamp 40 and thereby changing the ratio of the light quantity of the image of the presented optotype and the ambient light quantity thereof.

Figure 6A:
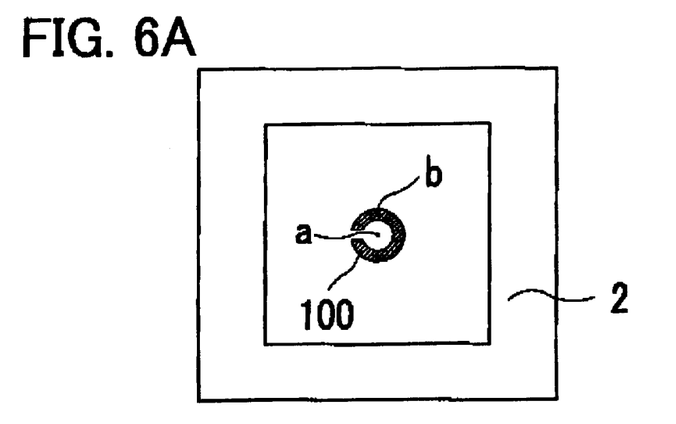
FIGS. 6A to 6C are explanatory views of images with contrast variations of optotypes to be presented for test.
Figure 6B:
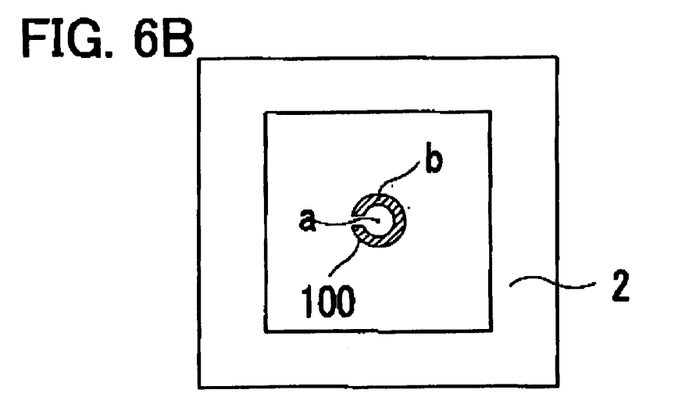
Figure 6C:
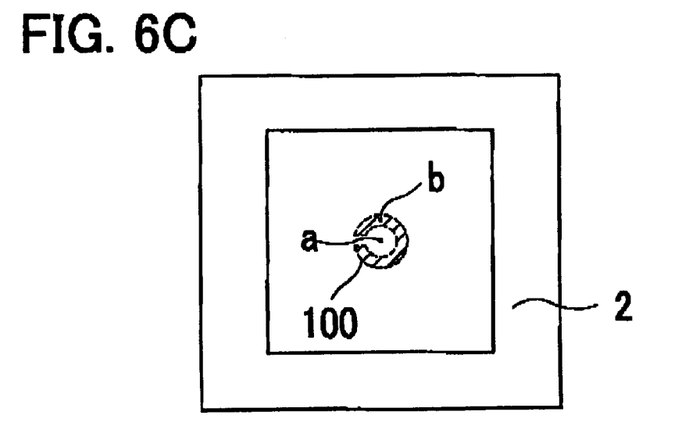

FIGS. 6A to 6C are views of the optotype image 100 presented to the eye E through the window 6. In the present embodiment, assuming the ambient brightness of the image 100 to be a(cd/m$^2$) and the brightness of same to be b(cd/m$^2$), the contrast ratio of the image 100 is expressed by (a−b)/(a+b)×100. For example, in the normal visual acuity test that the lamp 24 is turned on and the lamp 40 remains off, the brightness b of the image 100 becomes almost 0(cd/m2), presenting the image 100 with 100% contrast ratio (a state shown in FIG. 6A).

To change the contrast ratio to 25%, 12%, 6%, and others, the light quantity of the lamp 24 is reduced and that of the lamp 40 is increased, thereby changing the brightness values a and b. Thus, the contrast of the image 100 can be lowered as shown in FIGS. 6D and 6C. At the same time, the control section 70 controls each light quantity of the lamps 24 and 40 so that average brightness of the optotype image presenting planes becomes constant in order to maintain the light quantity (brightness) incident on the eye E constant even if the contrast ratio is changed.

To control those light quantities, a brightness meter is used to previously determine the needed light quantity (light quantity ratio) of each of the lamps 24 and 40 in correspondence with every contrast ratio. The illumination light quantity of each of the lamps 24 and 40 corresponding to each contrast ratio is determined in advance as follows; brightness at plural points of the presented optotype image (for example, a center, upper, lower, right, and left points on the image) is measured in each contrast ratio; and the illumination light quantity is increased/decreased as the light quantity ratio being maintained constant so that the average brightness in all the contrast ratios becomes constant.

It is to be noted that the total quantity of light reflected by the half mirror 28 to illuminate the eye E is adjusted to about 140 (cd/m2) in the present embodiment, which is not limited thereto. The light quantity may be adjusted within specifications for visual acuity test (80–320 (cd/m2) in an ISO standard).

Figure 7:
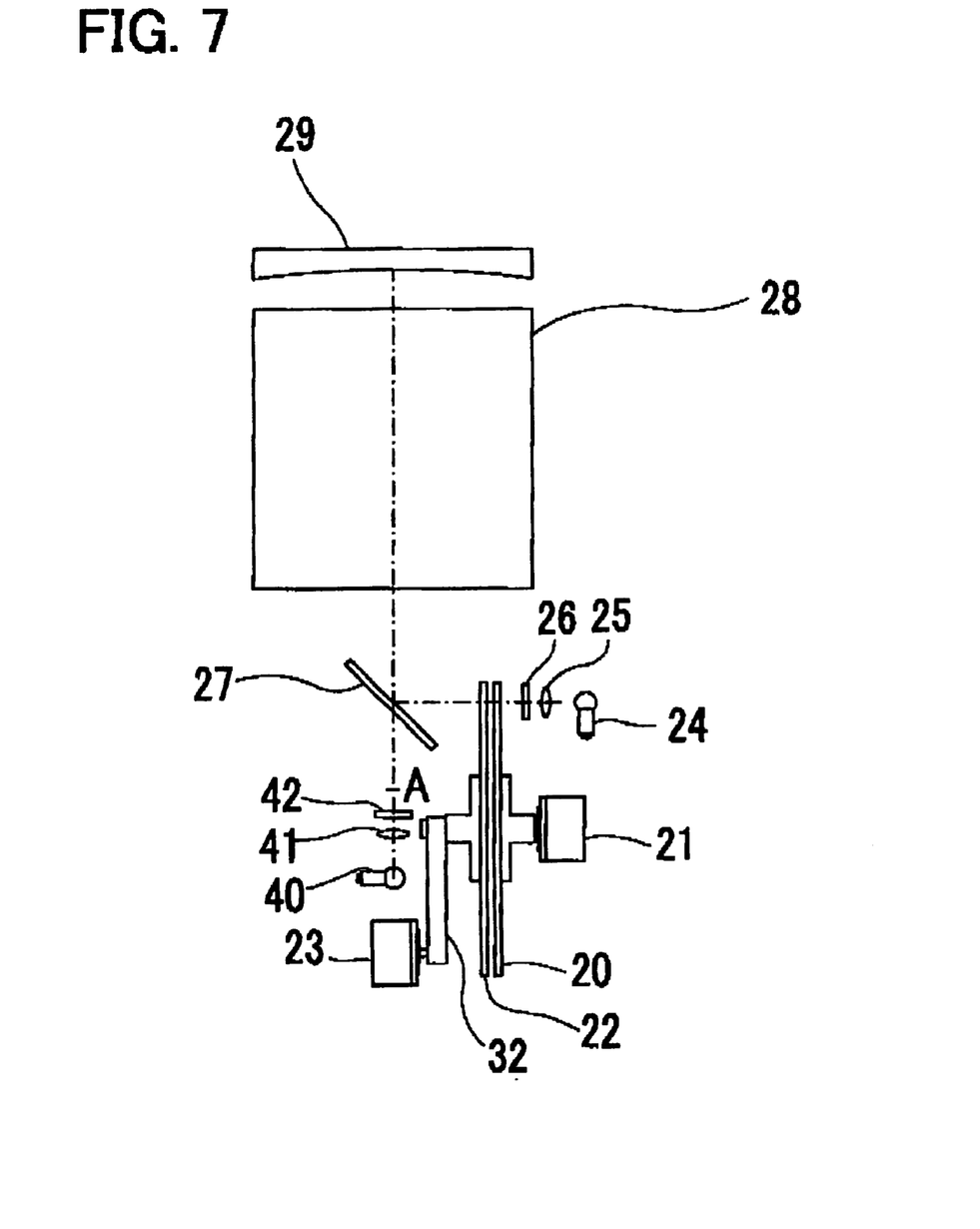
FIG. 7 is an alternative of the apparatus.

In the above embodiment, the mirror 43 is used for guiding the light from the lamp 40 to the half mirror 27. If the motor 23 and the mirror 43 structurally interfere with each other, a belt 32 may be additionally provided to rotate the mask disc 22 as shown in FIG. 7. In this case, the present invention can be achieved without use of the mirror 43.

Figure 8:
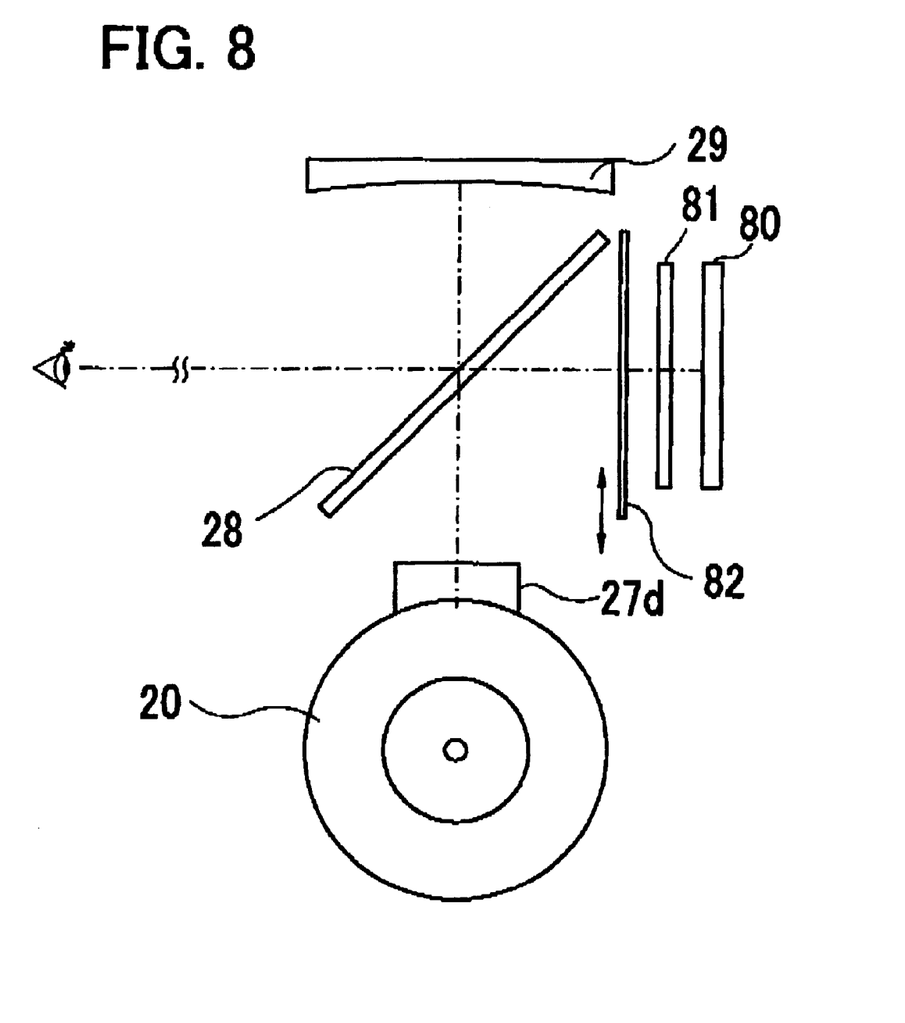
FIG. 8 is another alternative of the apparatus.

In the above embodiment, the light from the lamp 40 is made coaxial with the optotype light with use of the half mirror 27, which is not limited thereto. FIG. 8 is an alternative structure of the apparatus in which, without use of the half mirror 27, the half mirror 28 is also used for combining the background illumination light and the optotype light. In this case, a total reflection mirror 27d is disposed instead of the half mirror 27.

In the rear of the half mirror 28, there are disposed a surface light source 80 using a plurality of LCDs, a diffusing plate 81, and a black screen 82 for preventing reflection. The black screen 82 is placed between the half mirror 28 and the diffusing plate 81 during a normal visual acuity test (with a 100% contrast ratio), thereby preventing reflection of superfluous light.

During a contrast sensitivity test, the black screen 82 is held in a position off the front of the diffusing plate 81. The surface light source 80 and the lamp 24 are controlled to light up. Thus, the contrast ratio of the optotype image presented can be changed.

Figure 9A:
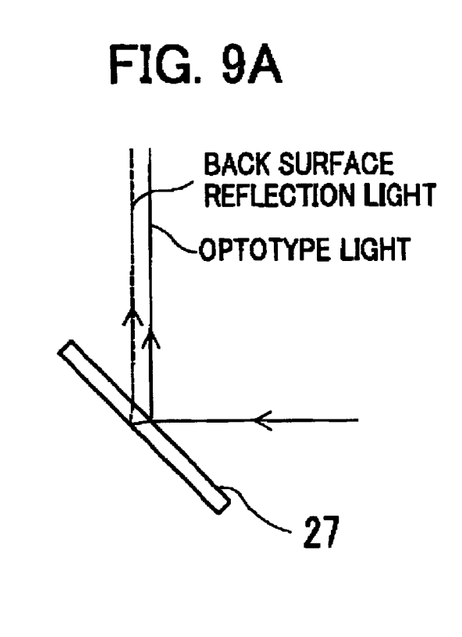
FIGS. 9A to 9C are explanatory views showing half mirrors for canceling a ghost image of an optotype image.
Figure 9B:
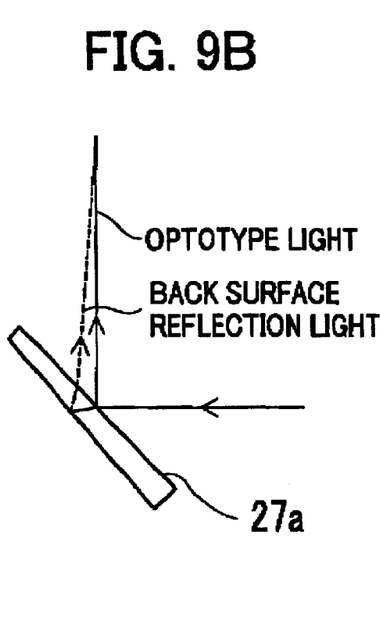
Figure 9C:
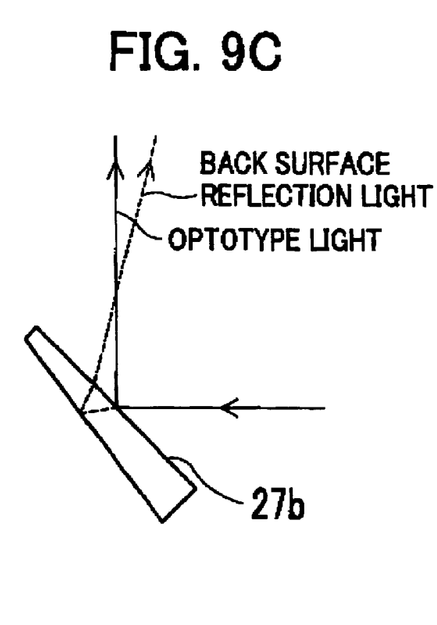

It is to be noted that the use of the half mirror 27 may make the test difficult occasionally because the back surface of the half mirror 27 facing the lamp 40 side reflects a part of the optotype light (see FIG. 9A), generating a ghost image of the optotype image, which is seen by the examiner. To prevent such inconvenience, as shown in FIGS. 9B and 9C, the half mirror 27 may be constructed to have a surface facing the lamp 40 side formed at a predetermined inclination angle, namely, in non-parallel, with respect to the other surface facing the lamp 24 side, thereby canceling a ghost image. FIG. 9B shows a half mirror 27a with a back surface formed at an inclination angle appropriate to reflect a part of the optotype light so that a ghost image coincides with the optotype image in order to cancel the ghost image. FIG. 9C shows another half mirror 27b with a back surface formed at an inclination angle appropriate to reflect a part of the optotype light so that a ghost image is formed outside the visual field of the eye E in order to cancel the ghost image. In those examples, the inclination angle of the surface facing the lamp 40 side with respect to the surface (having an inclination angle of 45 degrees with respect to the optical axis) facing the lamp 24 side is determined according to a thickness and a refractive index of the half mirror 27, a curvature of the concave mirror 29, a distance between the half mirror 27 and the concave mirror 29, and others.

The back surface facing the lamp 40 side will produce primary, secondary, and subsequent back surface reflection lights; however, the secondary and subsequent reflection lights have only a very small light quantity. In this example, therefore, only the ghost image formed by the primary reflection light is considered. Moreover, as with the half mirror 27, the half mirror 28 may be constructed to have a surface facing the lamp 40 (the surface light source 80) side formed at a predetermined inclination angle with respect to the other surface facing the concave mirror 29 side, in non-parallel.

In the above embodiment, the lamp 24 is arranged on a reflecting side of the half mirror 27 and the lamp 40 is arranged on a transmitting side of same. Those lamps 24 and 40 may be interchanged. In that case, the optotype disc 20 and the mask disc 22 are arranged horizontally.

As explained above, according to the present invention, a standalone type of an apparatus can perform both a visual acuity test and a contrast sensitivity test, thereby enhancing space savings.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A visual function test apparatus for testing a visual function by presenting an optotype to an examinee's eye, the apparatus including:
    a first half mirror disposed on a projection optical axis of light of the optotype;
    an illumination light source having a projection optical axis which is made substantially coaxial with the projection optical axis of the optotype light by the first half mirror;
    a concave mirror which reflects an illumination light from the illumination light source and the optotype light;
    a second half mirror disposed between the first half mirror and the concave mirror, the second half mirror reflecting the optotype light and the illumination light both reflected by the concave mirror toward the examinee's eye; and
    a control section which changes a ratio between a light quantity of the optotype light and a light quantity of the illumination light in accordance with a predetermined contrast ratio.

2. The visual function test apparatus according to claim 1 further including a rotating unit which rotates the second half mirror about an axis perpendicular to the projection optical axis of the optotype light.

3. The visual function test apparatus according to claim 1 further including a diffusing plate disposed between the first half mirror and the illumination light source.

4. The visual function test apparatus according to claim 3, wherein the diffusing plate is placed in a position closer to the illumination light source than a conjugate position with the optotype with respect to the concave mirror.

5. The visual function test apparatus according to claim 1, wherein the control section changes the light quantity of each of the optotype light and the illumination light so that average brightness of presented optotypes becomes almost constant.

6. The visual function test apparatus according to claim 1, wherein the first half mirror has a reflection surface on which a metallic half mirror coating is applied.

7. The visual function test apparatus according to claim 1, wherein the first half mirror has a surface facing a concave mirror side and another surface facing an illumination light source side, the surfaces being provided in non-parallel.

8. The visual function test apparatus according to claim 1 including an apparatus for testing a visual acuity and a contrast sensitivity of the examinee's eye.

9. A visual function test apparatus for testing a visual function by presenting an optotype to an examinee's eye, the apparatus including:
    a concave mirror which reflects light of the optotype;
    a half mirror which reflects the optotype light reflected by the concave mirror toward the examinee's eye;
    an illumination light source having a projection optical axis which is made substantially coaxial with a projection optical axis of the optotype light by the half mirror; and
    a control section which changes a ratio between a light quantity of the optotype light and a light quantity of an illumination light from the illumination light source in accordance with a predetermined contrast ratio.

10. The visual function test apparatus according to claim 9 further including a rotating unit which rotates the half mirror about an axis perpendicular to the projection optical axis of the optotype light.

11. The visual function test apparatus according to claim 9 further including a diffusing plate disposed between the half mirror and the illumination light source, the illumination light source including a surface light source.

12. The visual function test apparatus according to claim 11 further including a black screen removably disposed between the half mirror and the diffusing plate.

13. The visual function test apparatus according to claim 9, wherein the control section changes the light quantity of each of the optotype light and the illumination light so that average brightness of presented optotypes becomes almost constant.

14. The visual function test apparatus according to claim 9, wherein the half mirror has a surface facing a concave mirror side and another surface facing an illumination light source side, the surfaces being provided in non-parallel.

15. The visual function test apparatus according to claim 9 including an apparatus for testing a visual acuity and a contrast sensitivity of the examinee's eye.

* * * * *